United States Patent [19]

Kawashima

[11] Patent Number: 5,101,807
[45] Date of Patent: Apr. 7, 1992

[54] ENDOSCOPE CONNECTING APPARATUS

[75] Inventor: Masahiro Kawashima, Hino, Japan

[73] Assignee: Olympus Optical Co., Ltd., Tokyo, Japan

[21] Appl. No.: 465,684

[22] Filed: Jan. 16, 1990

[30] Foreign Application Priority Data

Oct. 2, 1989 [JP] Japan .................................. 1-31471
Oct. 2, 1989 [JP] Japan .................................. 1-31472

[51] Int. Cl.[5] .............................................. A61B 1/00
[52] U.S. Cl. ........................................... 128/6; 128/4; 385/43
[58] Field of Search ...................... 128/4–6; 350/96.20, 96.26

[56] References Cited

U.S. PATENT DOCUMENTS

| 4,527,551 | 7/1985  | Ishii          | 128/4     |
| 4,552,131 | 11/1985 | Omagari        | 128/6     |
| 4,553,814 | 11/1985 | Bahl et al.    | 350/96.20 |
| 4,667,655 | 5/1987  | Ogiu et al.    | 128/6     |
| 4,690,495 | 9/1987  | Giannini       | 350/96.20 |
| 4,738,508 | 4/1988  | Palmquist      | 350/96.20 |
| 4,742,818 | 5/1988  | Hughes et al.  | 128/6     |
| 4,782,819 | 11/1988 | Adair          | 128/6     |
| 4,844,071 | 7/1989  | Chew et al.    | 128/6     |
| 4,896,986 | 1/1990  | Terayama       | 128/4     |
| 4,947,828 | 8/1990  | Carpenter et al. | 128/6   |

FOREIGN PATENT DOCUMENTS

| 335531     | 10/1989 | European Pat. Off. ......... 350/96.2 |
| 59-232311  | 12/1984 | Japan . |
| 62-201134  | 9/1987  | Japan . |
| 63-272320  | 11/1988 | Japan . |
| 63-278016  | 11/1988 | Japan . |
| WO85/02101 | 5/1985  | World Int. Prop. O. . |

Primary Examiner—Stephen C. Pellegrino
Assistant Examiner—Ralph A. Lewis
Attorney, Agent, or Firm—Armstrong & Kubovcik

[57] ABSTRACT

The present invention is an image guide which is provided in an endoscope in order to transmit an object image observed by the endoscope. The image guide includes a connector having an emitting end surface of the image guide. An object image observing apparatus is removably connected to the connector so as to touch the connector. The object image observing apparatus has a forming image lens system for making an object image, transmitted from the image guide, be observable. A pressing member places the emitting end surface of the image guide in the focal position of the forming image lens system by pressing together the connector and the object image observing apparatus.

10 Claims, 9 Drawing Sheets

ENDOSCOPE CONNECTING APPARATUS

BACKGROUND OF THE INVENTION

The present invention relates to an endoscope connecting apparatus which transmits an object image.

Recently, a method has been used whereby, by attaching a television camera to an endoscope eyepiece optical system, a plurality of observers observe the same picture image using a monitor television. The picture image is recorded and repeatedly reproduced by a video system so that a highly precise diagnosis can be made.

In an endoscope, such as a blood vessel endoscope used during an operation, the above mentioned method has been used. However, this endoscope has a distinct clean area and an unclean area while using the endoscope during an operation. Generally, since a tool, such as a television camera, has a structure which cannot be disinfected and sterilized, the tool becomes an unclean area and an eyepiece part, being connected with the television camera, becomes an unclean area so that an operator cannot touch the eyepiece part. Thus, as shown in the Gazette of Japanese Patent Laid Open No. 232311/1984, an endoscope in which only an eyepiece part is separated from an operating part, which is frequently touched by an operator, is devised.

In order to make an endoscope simpler, smaller and lighter, in the Gazettes of Japanese Patent Laid Open No. 201134/1987 and Japanese Patent Laid Open No. 278016/1988, an eyepiece lens is removed from an endoscope and an image guide is directly connected to a television camera so as to form an object image. In U.S. Pat. No. 4,624,243, an endoscope in which an eyepiece and an inserting part can be removed is shown.

When an image guide is connected to a television camera or an eyepiece part, an image transmitted by the image guide enters a receiving light surface of the solid state imaging device or an eyepiece optical system. It is, therefore, necessary to make the optical axis on the side of the image guide correspond to the optical axis a) on the television camera or b) on the side of the eyepiece part so as to avoid losing a part of a border of the image.

Unless the end surface of the image guide is located on a focal position of a forming image lens system on an observing side, an object image which is in focus cannot be obtained. Therefore, it is necessary to make the distance between the television camera and the image guide always be equal to the distance between the side of the eyepiece part and the image guide.

In the above mentioned prior art of the Gazette of Japanese Patent Laid Open No. 278016/1988, this point however is not stated. In the Gazette of Japanese Patent Laid Open No. 201134/1987, a connector is removably held and fixed by a click mechanism. However, a positive means for making the optical axes and distances equal is not provided.

In U.S. Pat. No. 4,624,243, because an eyepiece is screwed into an inserting part, or vice versa, there is a problem that an optical axis of an image guide is not positioned on an optical axis of a forming image optical system due to misalignment between the screwed parts.

Furthermore, because of the misalignment of the screwed parts, it is impossible to focus the eyepiece so that a focusing mechanism must be provided in the forming image lens system and the focus needs to be adjusted by an operator for each operation, therefore, the operation of the device is complicated.

OBJECT AND SUMMARY OF THE INVENTION

The object of the present invention is to provide an endoscope connecting apparatus having a simple formation in which attachment and removal are easily carried out. An optical axis of an image guide can accurately correspond to an optical axis of an object image observing means. Also, an end surface of an image guide fiber can be accurately placed in a focal position of a forming image lens system of the object image observing means.

The endoscope connecting apparatus of the present invention is an image guide which is provided in an endoscope in order to transmit an object image observed by the endoscope and comprises a connector including an emitting end surface of the image guide, an object image observing apparatus removably connected to the connector so as to touch the connector including a forming image lens system for making an object image transmitted from the image guide be observable and a pressing member for placing the emitting end surface of the image guide in the focal position of the forming lens system by pressing a touching surface between the connector and the object image observing apparatus.

BRIEF DESCRIPTION OF THE DRAWINGS

FIGS. 1 to 9 relate to the first embodiment of the present invention.

DETAILED DESCRIPTION OF THE PREFERRED EMBODIMENTS

Embodiments of the present invention will be explained by referring to the drawings as follows:

FIGS. 1 to 9 show the first embodiment of the present invention.

Figure 1:
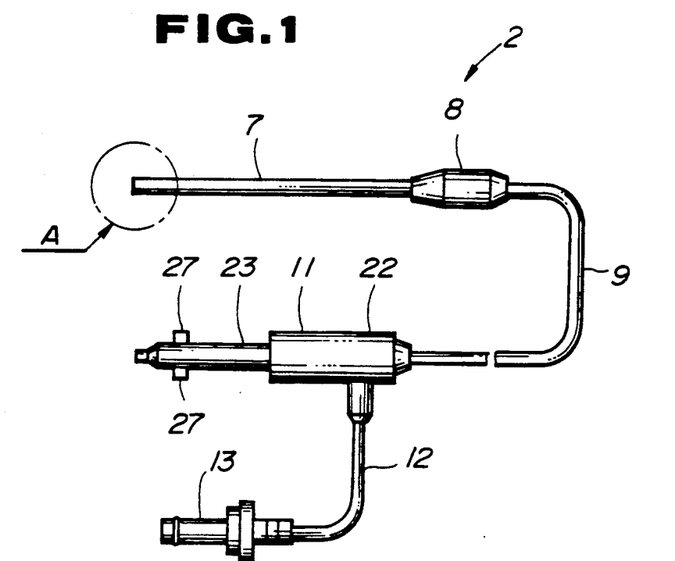
FIG. 1 is an explanatory view showing a blood vessel endoscope.
Figures 2, 4:
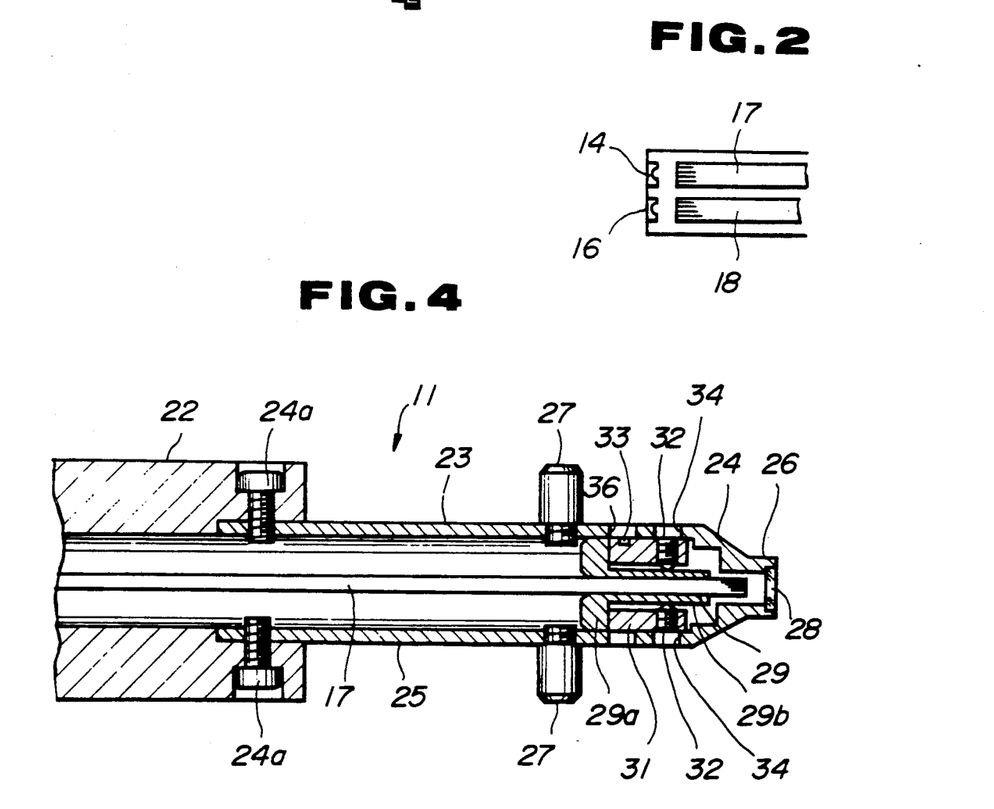
FIG. 2 is a detailed view showing a part in FIG. 1.
FIG. 4 is a sectional view of a connector.
Figure 3:
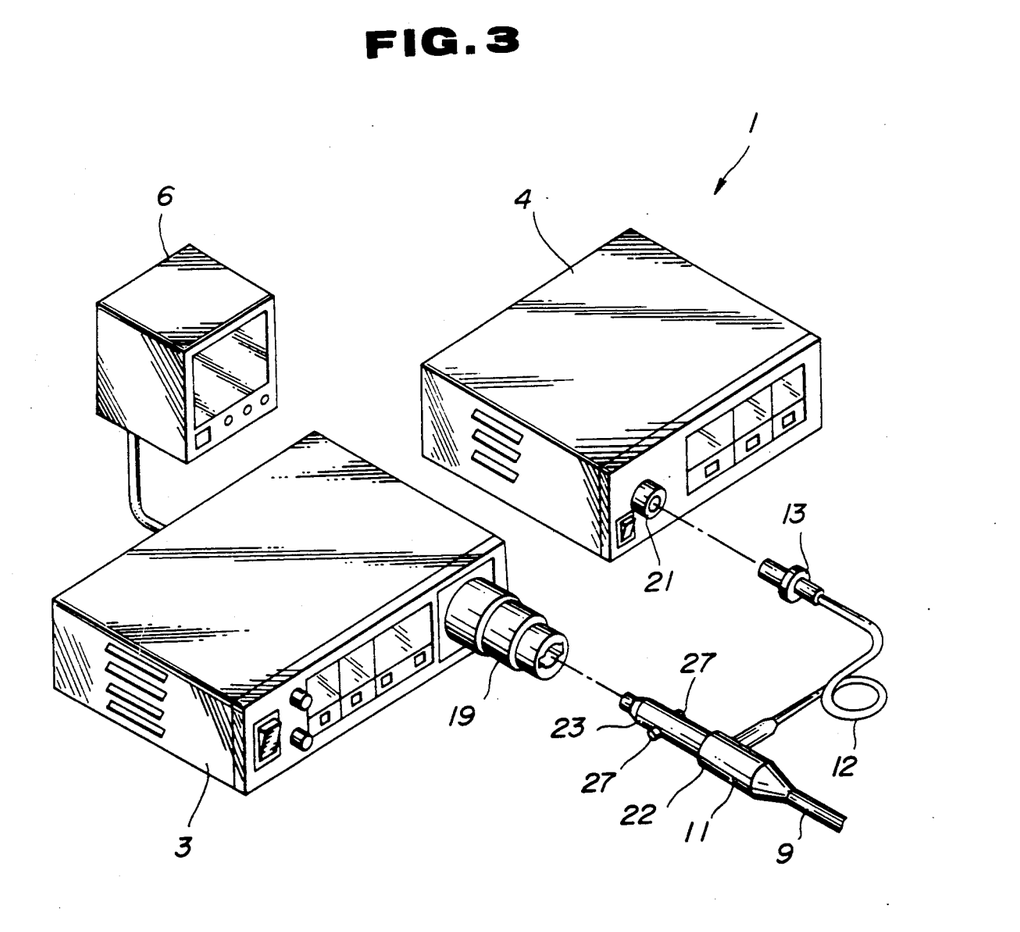
FIG. 3 is an explanatory view of fitting apparatuses to which a blood vessel endoscope is connected.

In FIGS. 1 to 3, an endoscope apparatus 1 of the present embodiment consists of a blood vessel endoscope 2, a television camera apparatus 3 to which the blood vessel endoscope 2 is connected, a light source apparatus 4 which supplies illuminating light to the blood vessel endoscope 2 and a monitor 6 which displays an endoscope image obtained from the blood vessel endoscope 2.

The above mentioned blood vessel endoscope 2 consists of a bendable elongated inserting part 7 and a holding part 8 which is provided at the distal end of the inserting part 7. Also, a universal cord 9 is extended from the distal end of the holding part 8 and an image guide connector 11 is provided at the distal end of the universal cord 9. Extending from a side of the image guide connector 11, is a light guide cord 12. A light guide connector 13 is provided at the distal end of the light guide cord 12.

As shown in FIG. 2, an objective lens 14 and a light distributing lens 16 are provided at the tip surface of the above mentioned inserting part 7. An incident end surface of an image guide fiber 17, which transmits an object image, is provided at the focal position of the objective lens 14. The image guide fiber 17 is inserted through the inserting part 7, the holding part 8 and the universal cord 9 and reaches the image guide connector 11. At the rear of the light distributing lens 16, an emitting end surface of a light guide fiber 18, which transmits illuminating light, is provided. The light guide fiber 18 passes through the inserting part 7, the holding part 8, the universal cord 9, the image guide connector 11 and the light guide cord 12 and reaches the light guide connector 13.

The above mentioned image guide connector 11 is removably connected to a socket part 19 of the above mentioned television camera apparatus 3. When the image guide connector 11 is connected to the socket part 19, the direction of the light guide cord 12 will correspond to the direction of a light source socket part 21 of the light source apparatus 4. The light source apparatus 4 is provided on one side of the television camera apparatus 3 so that the light guide connector 13 can be easily connected to the light source socket part 21.

The above mentioned light source apparatus 4 includes a light source part (not illustrated) which radiates illuminating light and will supply the illuminating light to an incident end surface of the light guide fiber 18 which is provided in the light guide connector 13 which is connected to the light source socket part 21.

The above mentioned television camera apparatus 3 includes a television camera (not illustrated). An object image from the objective lens 14 is transmitted by the image guide fiber 17 through the image guide connector 11 and will enter the television camera.

In the television camera apparatus 3, the object image from the image guide fiber 17 is electrically converted and processed by predetermined signal processing to display an endoscope image on the monitor 6.

In FIG. 4, the above mentioned image guide connector 11 consists of a) a main body part 22 which is held when an operator connects the image guide connector 11 to the socket part 19 and b) a socket inserting part 23, which is thinner in diameter than the diameter of the main body part. The socket inserting part 23 is inserted into the socket part 19 of the camera 3.

The above mentioned main body part 22 and the socket inserting part 23 are tubular in form. The socket inserting part 23 is fitted inside the main body part 22 and is fixed by screws 24a.

A taper part 24 is in the form of a thin diameter in the direction of the tip and is provided at the tip part of the socket inserting part 23. A thin diameter part 26 is formed on one end of the tip of the taper part 24.

A thick diameter part 25 is an outer wall extending from the other end of the taper part 24 to the socket inserting part 22. Pins 27 and 27 are spirally fitted to the thick diameter part 25 so as to be projected in the direction of the diameter at an angle of 180 degrees with each other.

A cover glass 28 is fitted to the tip surface of the socket inserting part 23 so that dust can not enter within the socket inserting part 23. The above mentioned image guide fiber 17 is inserted in the socket inserting part 23 sealed up by the cover glass 28 so that the emitting end surface of the image guide fiber 17 opposes the above mentioned cover glass 28. On the tip part of the image guide fiber 17, a flange part 29a is fixed within the main body part 22 and an image guide holding member 29, on which a thin diameter holding part 29b is formed, is fixed on the tip part of a binding agent or the like.

Centering screws 32 and 32 are spirally fitted in the direction of the diameter so as to have an angle of 180 degrees with a tubular centering member 31. The tubular centering member 31 is slidably provided on the inner wall of the socket inserting part 23 so that the tip parts of the centering screws 32 touch the wall of the above mentioned holding part 29b. The center of the optical axis of the image guide fiber 17 is adjusted by loosening one of the centering screws 32 and driving the other centering screw 32.

An adjustment hollow part 33 moves the centering member 31 in the lengthwise direction and is provided on the side which is the outer wall of the above mentioned centering member 31 from the centering screw 32 to the side of the main body part 22. A hole 36 is provided at the position on the wall of the socket inserting part 23 which opposes the position where the adjustment hollow part 33 is provided. Holes 34 and 34 are provided at the positions on the wall of the socket inserting part 23 which opposes the positions where the above mentioned centering screws 32 and 32 are provided.

Figure 5:
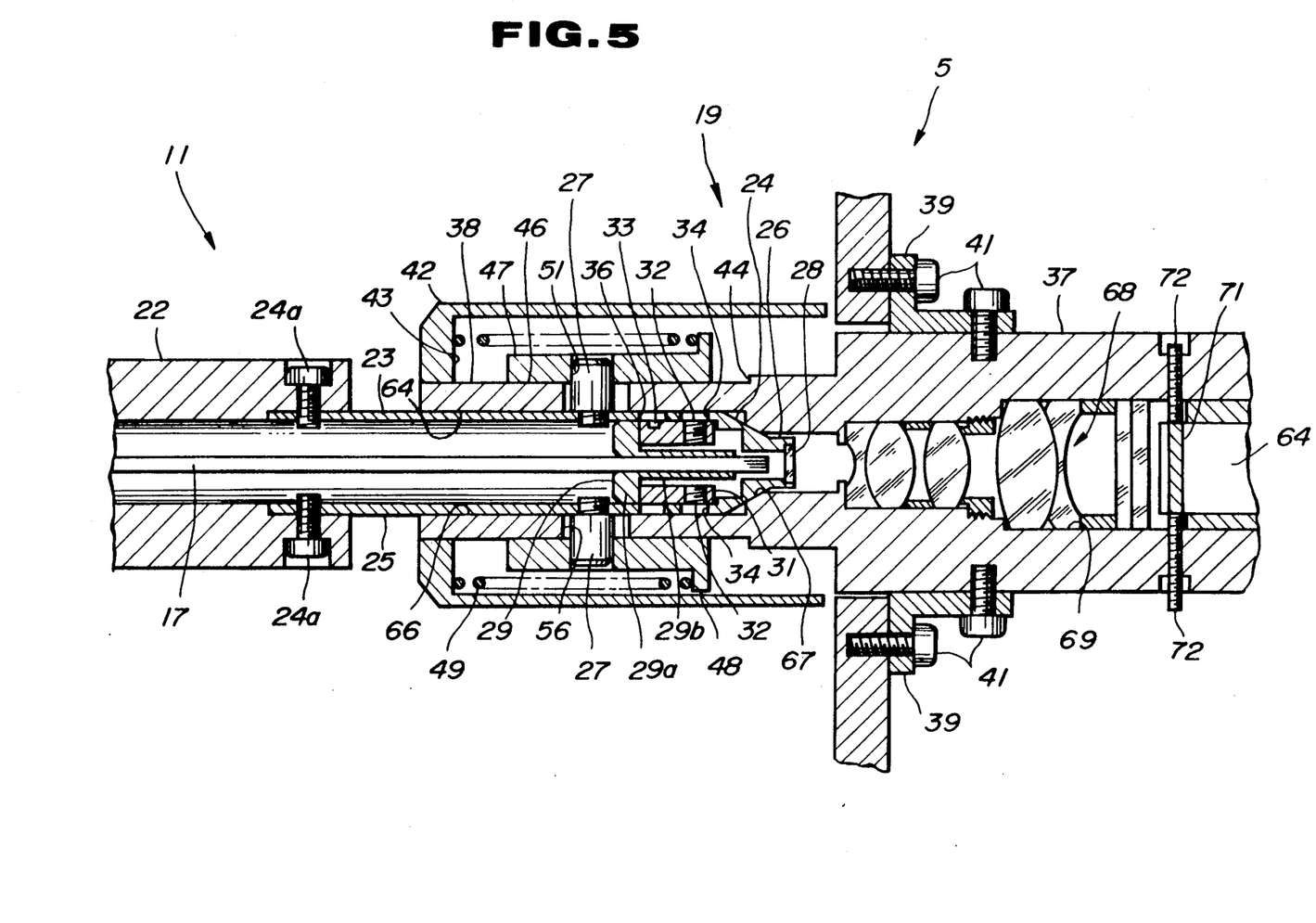
FIG. 5 is a sectional view showing the whole formation of an endoscope connecting apparatus.

In FIG. 5, the socket part 19, which is provided in the television camera apparatus 3, consists of a thick diameter part 37 and a thin diameter part 38. The socket part 19 is fixed by screws 41, 41 ... through fitting members 39 and 39 so as to place the thick diameter part 37 within the television camera apparatus 3 and so as to expose the thin diameter part 38 outside the television camera apparatus 3.

The circumference of the above mentioned thin diameter part 38 is covered with an almost cylindrical cover member 42 so as to include a space between the thin diameter part 38 and this cover member 42. The end on the side of the connector 11 of the cover member 42 is blocked up so as to form a wall part 43.

On the thin diameter part 38, a sliding part 46 is formed on the side of the connector 11 by a difference in level part 44. On the sliding part 46, an almost cylindrical cam ring 47 is slidably provided. A flange part 48 is circularly provided on the outer wall of the cam ring 47 on the side of the cam ring 47 toward the television camera apparatus 3. As a pressing means, a coil spring 49 is pushed and provided between the flange part 48 and above mentioned wall part 43. On the cam ring 47, the flange part 48 and the difference in level part 44 touch by pressure from the coil spring 49 when the connector 11 is not connected to the socket part 19.

Figure 7:
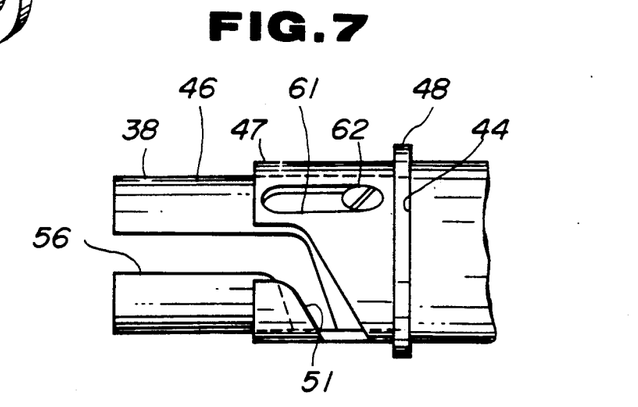
FIG. 7 is a view in the direction of the arrow B-B' in FIG. 6.
Figure 8:
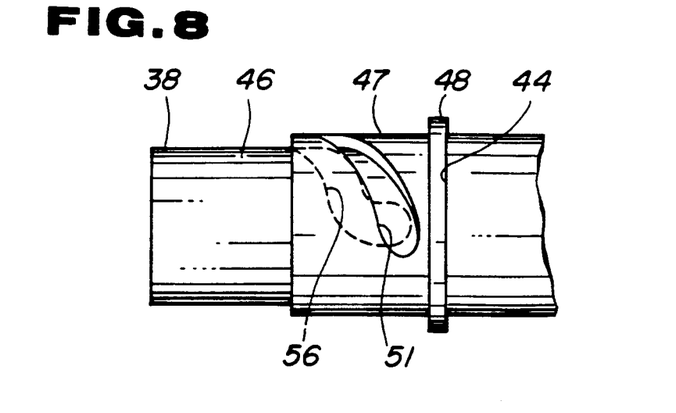
FIG. 8 is a view in the direction of the arrow C-C' in FIG. 6.

As shown in FIG. 7, a long hole 61 is provided in the lengthwise direction on the wall of the cam ring 47 and a pin 62, which is projected in the direction of the diameter of the sliding part 46, is inserted in the long hole 61. The rotary movement of the cam ring 47 is controlled by the pin 62 and long hole 61.

In FIGS. 6 to 9, cam grooves 51 and 51 are provided on the above mentioned cam ring 47. These cam grooves 51 and 51 consist of continuous lengthwise groove part 53, oblique groove part 54 and horizontal groove part 55. The lengthwise groove part 53 has an opening on the cam ring 47 toward the side of connector 11. Also, cam grooves 56 and 56 are provided on the sliding part 46 and consists of continuous lengthwise groove part 57, oblique groove part 58 and horizontal groove part 59. The lengthwise groove part 57 has an opening on the sliding part 46, the side of the connector 11. A part of the oblique groove part 58 of the sliding part 46 is blocked up by the cam ring 47 as shown in FIG. 9(a) when the connector 11 is not connected. When the connector 11 is connected, the connector 11 is rotated so that the pin 27 touches a slope 63 on the side of the cam ring 47.

A through hole part 64 is provided in the socket part 19. A socket inserting hole 66 of the socket part 19 has an inner diameter which is a little thicker than the outer diameter of the thick diameter part 25 of the socket inserting part 19. The taper part 24 of the socket inserting part 23 is inserted and touches the hole part 64 from the side of the connector 11. The hole part 64 has the taper part 24 inserted thereto. The hole part 64 includes a taper hole 67 which has almost the same taper angle as the taper part 24 and a lens hole 69 which is supplied with a forming image lens system 68. The forming image lens system 68 forms an object image transmitted by the above mentioned image guide fiber 17.

The center of the above mentioned taper hole 67 is provided so as to correspond to the optical axis of the forming image lens system 68.

In the focal position of the forming image lens system 68 within the above mentioned lens hole 69, an imaging surface of a solid state imaging device 71, which is an object image observing means, is provided. In order to make the optical axis of the forming image lens system 68, which is spirally fitted in the direction of the diameter of the socket part 19, correspond with the optical axis of the solid state imaging device 71, the tip parts of adjusting screws 72 and 72 touch the side of the solid state image device 71. The optical axis is adjusted by loosening one of the adjusting screws 72 and driving the other adjusting screw 72.

The operation of an endoscope connecting apparatus 5 which is formed as mentioned above will be explained as follows.

The optical axis of the image guide fiber 17, inserted in the image guide connector 11, is adjusted as follows.

If one of the centering screws 32, spirally fitted to the centering member 31, is loosened and the other centering screw 32 is spirally driven, the image guide fiber 17 is pressed in the spirally fitted direction through the holding member 29 so that the optical axis moves and the optical axis of the image guide fiber 17 and the center line of the connector 11 are adjusted.

A rod shaped tool is inserted in the adjustment hollow part 33 through the hole 36 and the holding member 29 is moved by way of the centering member 31 so that the emitting end surface of the image guide fiber 17 is moved in the lengthwise direction.

As mentioned above, the optical axis of the image guide connector 11 is adjusted.

In the case in which an image guide connector 11 is connected to the television camera 3, the connector 11 is pushed into the socket inserting hole 66 of socket 19 so as to put the pin 27 of connector 11 in a) the hole which is formed with cam grooves 56 of the sliding part 46 and b) a slit (not illustrated) provided at the end surface of the side of the connector 11 of the cover member 42.

In FIG. 9, if the pin 27 passes through the lengthwise groove part 57 and comes to the oblique groove part 58, the pin 27 presses the slope 63 of the oblique groove part 54 of the cam ring 47. Although the cam ring 47 is pressed toward the television camera apparatus 3 by the coil spring 49, the pin 27 moves the cam ring 47 in the direction of arrow D as shown in FIG. 9(b) so that the pin 27 pushes the coil spring 49 by rotating the connector 11. By further rotating the connector 11, the pin 27 pushes the cam ring 47 in the direction of arrow D along the oblique groove part 58 and comes to the lengthwise groove part 59 as shown in FIG. 9(c) so as to make the coil spring 49 elastic. If the hold of the connector 11 is lost in this place, the horizontal groove part 55 on the side of the cam ring 47 pushes the pin 27 in the direction of arrow E by the elasticity of the coil spring 49 and moves the pin 27 to the inner end of the lengthwise groove part 59 on the side of the sliding part 46. At the same time that the pin 27 moves to the inner end of the lengthwise groove part 59, the taper part 24 touches the taper hole 67. The taper angles of the taper part 24 and the taper hole 67 are almost the same and the center of the connector 11, that is, the optical axis of the image guide fiber 17 and the optical axis of the forming image lens system 68 correspond caused by the coil spring 49 pressing the taper part 24 against the taper hole 67. The end surface of the image guide fiber 17, in the connector 11, is placed in the focal position of the forming image lens system 68.

By the correspondence of the axes as mentioned above, the object image is centered on the imaging surface of the solid state imaging device 71 and the object image in focus is formed on the imaging surface of the solid state imaging device 71 by placing the end surface of the image guide fiber 17 in the focal position so that a normal and clear endoscope image is displayed on the picture of the monitor 6.

Figure 9A:
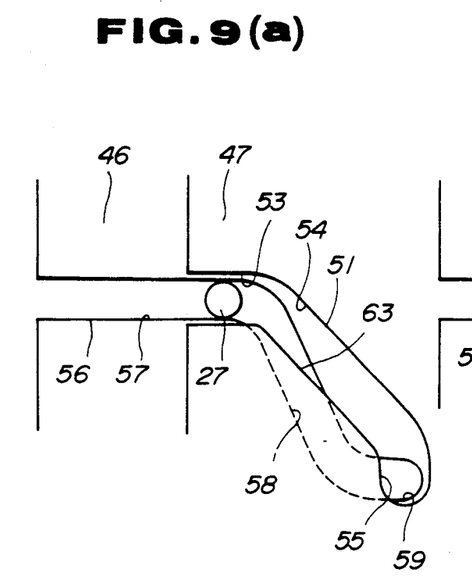
FIGS. 9(a)-9(d) are explanatory views where a connector part and a socket part are connected.
Figure 9B:
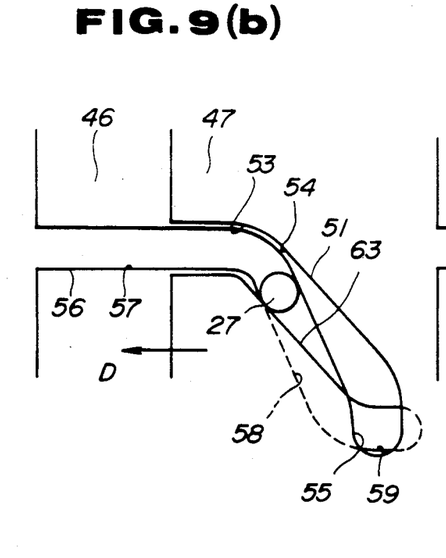
Figure 9C:
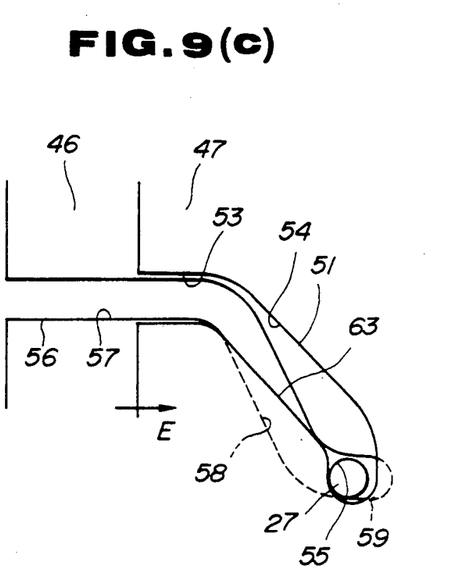
Figure 9D:
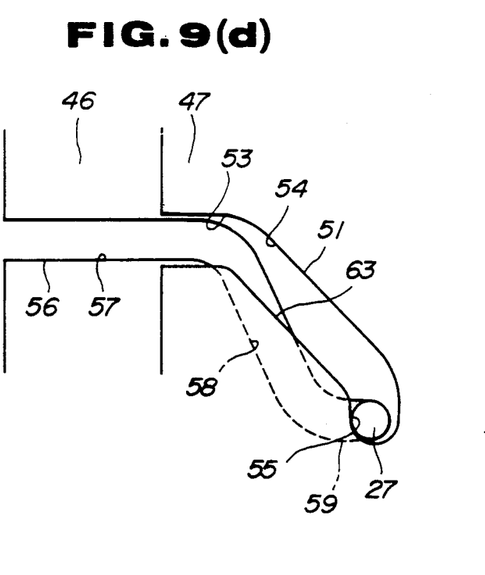

When an external force is applied to the connector 11 so as to pull out the connected connector 11, the elasticity of the coil spring 49 and the oblique groove part 58 prevent the connector 11 from being pulled out.

When the external force is applied to the connector 11 so as to rotate the connector 11, the lengthwise groove part 59 prevents the connector 11 from rotating.

In the case in which the connector 11 is removed from the television camera apparatus 3, first, the connector 11 is pulled and the pin 27 is pulled up to the oblique groove part 58 and then, the connector 11 is rotated. By this operation, the connector 11 can be removed from the socket part 19.

As mentioned above, in this embodiment, the taper part 24 is provided on the socket inserting part 23 and the taper hole 67 is provided in the socket part 19 so that the optical axis of the connector 11 can easily correspond with the optical axis on the socket part 19 by pressing the taper part 24 and the taper hole 67 by the coil spring 49. The end surface of the image guide fiber can be placed in the focal position of the forming image lens system 68.

Figure 6:
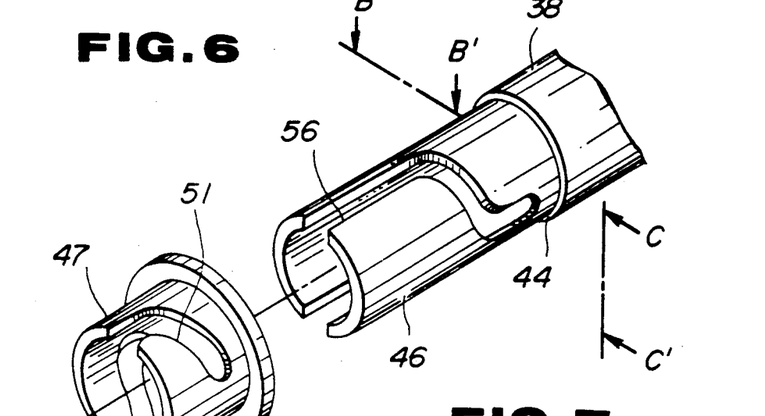
FIG. 6 is a perspective view of a cam ring and a socket part.

Since the cam grooves 51 and 56 are provided, the television camera apparatus 3 can be easily connected by only inserting the connector 11 with one hand and rotating the connector.

Since the end surface of the image guide can be placed in the predetermined position by a pressing means, complicated focusing operations become unnecessary and the endoscope connecting apparatus can be easily manipulated.

Also, because a lens control mechanism for focusing does not need to be provided, the formation of the apparatus becomes simple.

Figure 10:
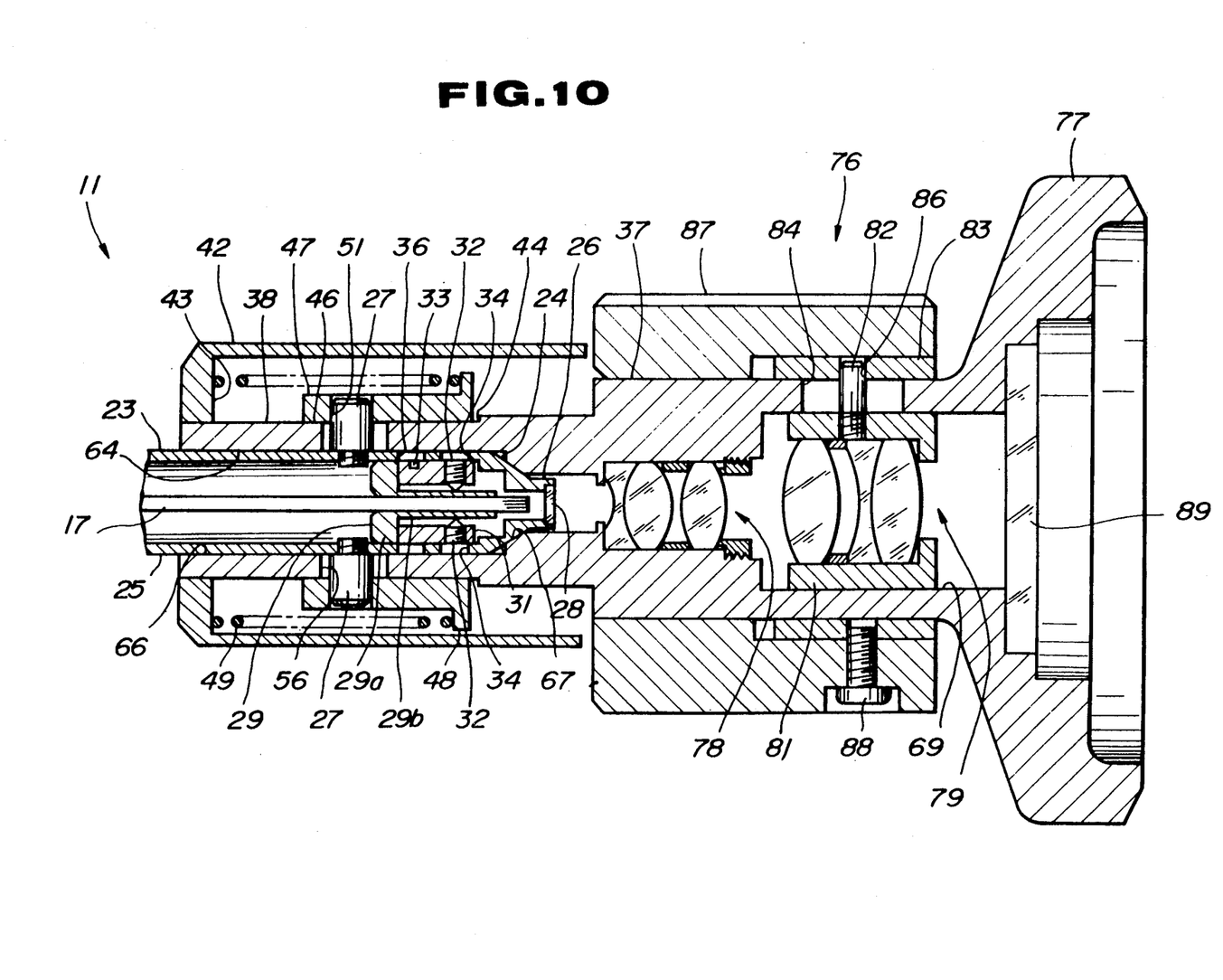
FIG. 10 relates to the second embodiment of the present invention and is a sectional view of an endoscope connecting apparatus which is connected to an eyepiece part.

FIG. 10 shows the second embodiment of the present invention.

The formation of the image guide connector 11 of this embodiment is the same as in the first embodiment. Also, since a part of the formation of the eyepiece part 76 is the same as in the formation of the thin diameter part 38 in the first embodiment, the same reference numerals are given to the same members and an explanation thereof will be omitted.

An eyepiece part 76, as an object observing means, consists of the thin diameter part 38, the thick diameter part 37 and an eyepiece 77 in that order from the side of the connector 11. On the thick diameter part 37, an eyepiece lens system 78 and a group of adjusting lenses 79 are provided so as to correspond with the optical axis of the connector 11 being connected. The group of adjusting lenses 79 is tubular-shaped and fixed within a movable ring 81 which is slidably provided in the lens hole 69. A pin 82 is spirally fitted in the outer wall of the movable ring 81 so as to be projected in the direction of the diameter. The pin 82 penetrates a long hole 84 which is provided in the lengthwise direction on the outer wall of the thick diameter part 37. A part which is projected over the thick diameter part 37 of the pin 82 is inserted in a cam groove 86 provided in the tubular cam ring 83 which is rotatably provided in the thick diameter part 37. The cam groove 86 is slantingly provided in the lengthwise direction. The cam ring 83 is fitted in an adjusting ring 87 and the thick diameter part 37, and fixed to the adjusting ring 87 by a screw 88. Also, the adjusting ring 87 is rotatably provided on the thick diameter part 37.

A cover glass 89 is fitted in the above mentioned eyepiece 77. Through the cover glass 89, an object image is observed by the naked eye of an observer.

The eyepiece 77 is shaped to be able to attach an exterior imaging apparatus and so on.

The eyepiece part 76 in this embodiment is connected to the connector 11 the same as in the first embodiment.

By the adjusting ring 87, the focus can be adjusted. That is, by rotating the adjusting ring 87, the cam ring 83, which is fixed in the adjusting ring 87, rotates and is inserted into the cam groove 86 of the cam ring 83 so that the pin 82, of which rotary movement is regulated by the long hole 84, moves in the lengthwise direction. Therefore, the movable ring 81 moves in the lengthwise direction so that the focus can be adjusted.

In this embodiment, the eyepiece part 76 can be easily connected to the connector 11.

As shown in the first embodiment, an endoscope image can be easily observed by the naked eye of an observer without using the television camera apparatus 3 and the monitor 6.

Furthermore, an image is observed not only by the naked eye, but also by a cinecamera or camera which can be connected to the eyepiece 77 so that the apparatus can be widely utilized.

The other formation, operations and effects are the same as in the first embodiment.

Figure 11:
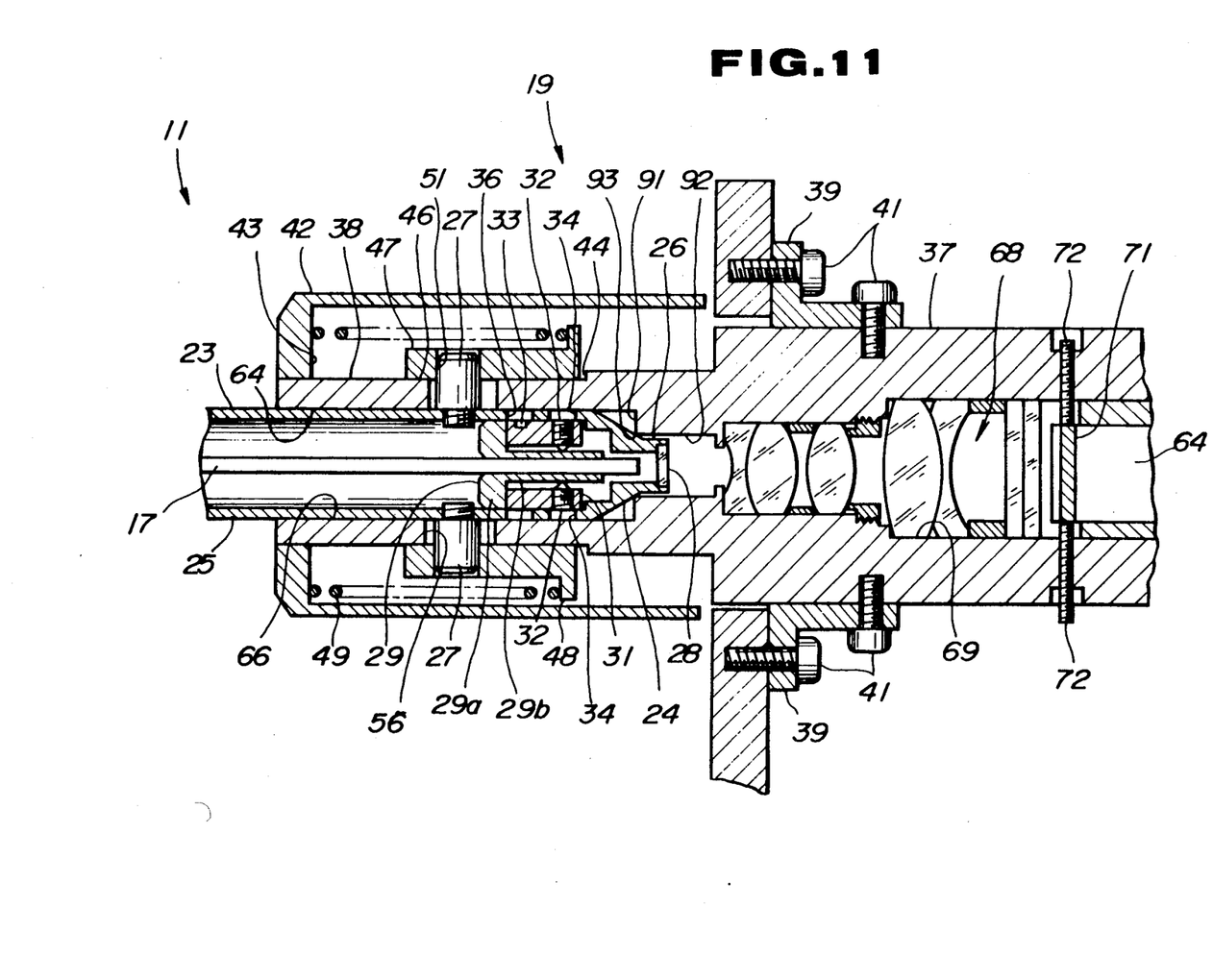
FIG. 11 relates to the third embodiment of the present invention and is a sectional view of an endoscope connecting apparatus.

FIG. 11 shows the third embodiment of the present invention.

In this embodiment, the present invention is applied to the connection with the television camera apparatus 3 as shown in the first embodiment.

In this embodiment, the taper hole 67 of the first embodiment is replaced with a difference in level part 91. Since the other formations are the same as in the first embodiment, the same reference numerals are given and an explanation thereof will be omitted.

In the hole part 64 of the socket part 19 of this embodiment, a) the socket insert hole 66, b) a thin diameter part 92 which is formed to be a thinner diameter than the diameter of the socket inserting part 66 in the difference in level part 91 and c) the lens hole 69 supplied with the forming image lens system 68, are provided in that order from the side of the connector 11.

In this embodiment, if the connector 11 is inserted into the socket inserting hole 66, the taper part 24 touches a fringe part 93 which is formed with the difference in level part 91 and the thin diameter part 92, and the taper part 24 is pressed by the coil spring 49. Then, the taper part 24 is continued to be pressed. The optical axis of the image guide fiber 17 and the optical axis of the forming lens system correspond by being pressed by the coil spring 49. An object image, without lacking a part of a boarder of the image, is formed on the imaging surface of the solid state imaging device 71.

Since a taper is processed only on the side of the connector 11 is adequate for this embodiment, the same effect as in the first embodiment can be obtained at a low cost.

The other formations, operations and effects are the same as in the first embodiment.

Figure 12:
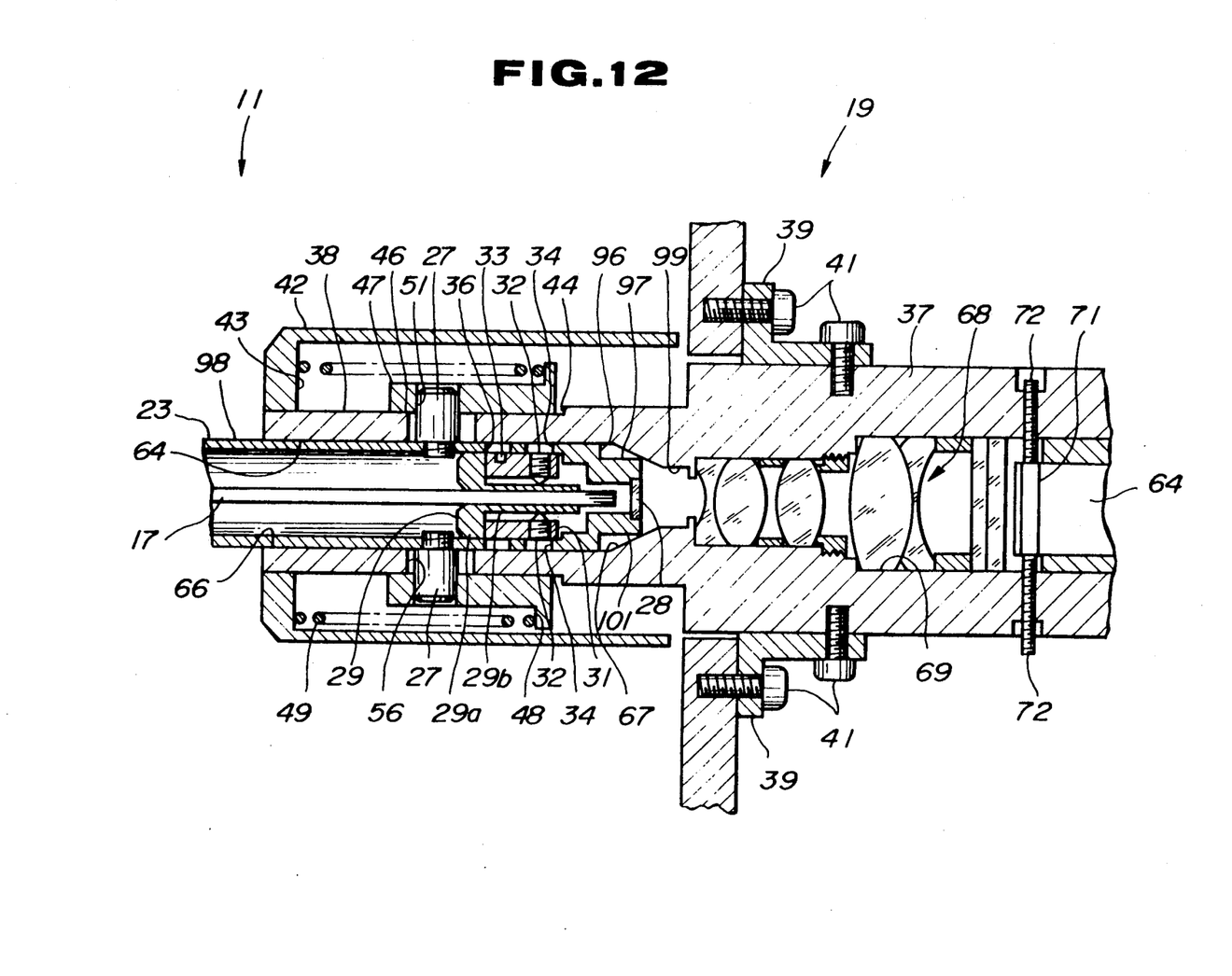
FIG. 12 relates to the fourth embodiment of the present invention and is a sectional view of an endoscope connecting apparatus.

FIG. 12 shows the fourth embodiment of the present invention.

In this embodiment, the present invention is applied to the endoscope connecting apparatus in order to connect with the television camera apparatus 3 the same as in the first embodiment.

In this embodiment, the taper part 24 of the first embodiment is replaced with a difference in level part 96. Since the other formations are the same as in the first embodiment, the same reference numerals are given and an explanation thereof will be omitted.

The socket inserting part 23 of the connector 11 of this embodiment consists of a thin diameter part 97, the difference in level part 96 and a thick diameter part 98 in that order from the tip part. The outer diameter of the thin diameter part 97 is thicker than the inner diameter of the hole part 99 which is placed between the taper hole 67 on the side of the socket part 19 and the lens hole 69.

In this embodiment, if the connector 11 is inserted into the socket inserting hole 66, a fringe part 101 is formed with the tip surface of the socket inserting part 23 and the thin diameter part 97 touches the taper hole 67. The fringe part 101 and the taper hole 67 are pressed by the coil spring 49 and kept in a pressed state. By being pressed by the coil spring 49, the optical axis of the image guide fiber 17 and the optical axis of the forming image lens system 68 correspond so that an object image, without a part of the image missing, is formed on the imaging surface of the solid state imaging device 71.

The other formations, operations and effects are the same as in the first embodiment.

Figure 13:
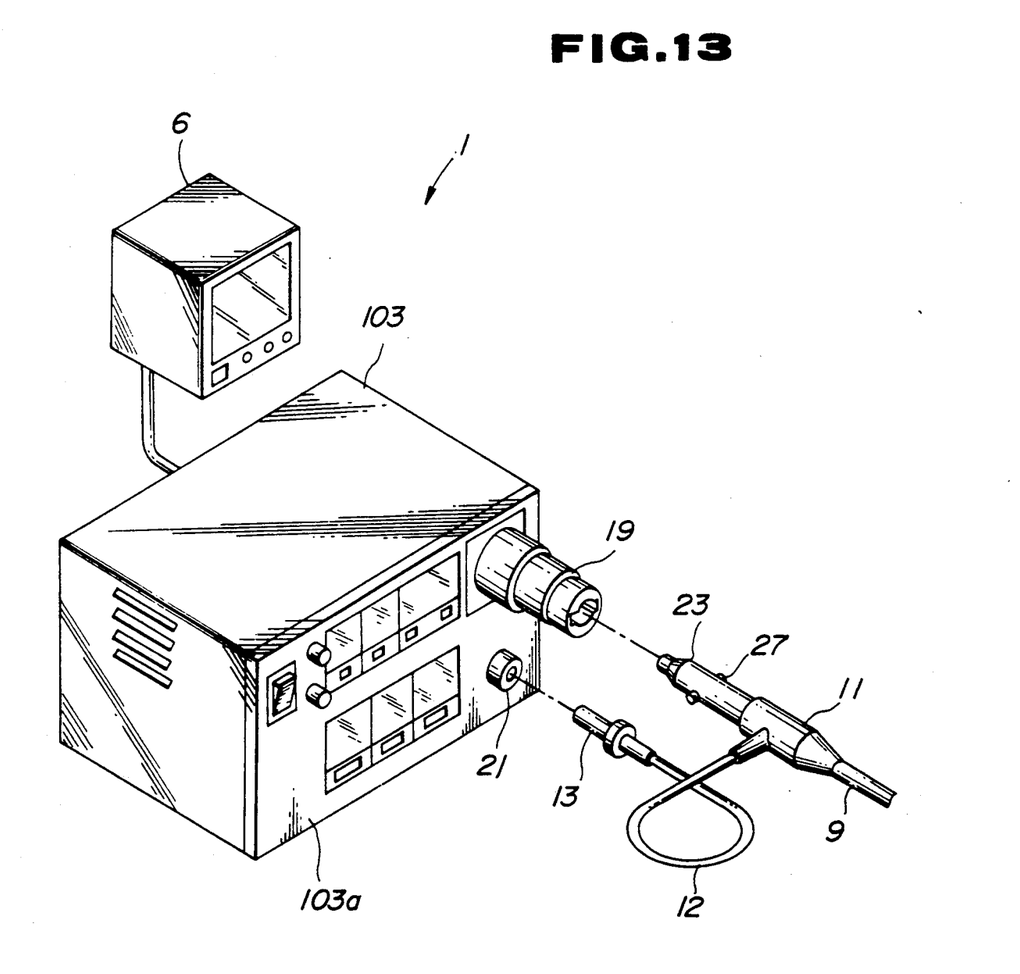
FIG. 13 relates to the fifth embodiment of the present invention and is an explanatory view showing a television camera apparatus to which a light source apparatus is joined.

FIG. 13 shows the fifth embodiment of the present invention.

Contrasted with each above mentioned embodiment in which the television camera apparatus 3 is kept separate from the light source apparatus 4, the television camera apparatus and the light source apparatus are joined together in this embodiment.

In a control apparatus 103 of this embodiment, the television camera apparatus 3 and the light source apparatus 4 are provided. The socket part 19 which is related to the television camera, a switch, a display light and others are provided on the upper part of an operation panel 103a and a light source socket part 21 which is related to the light source, a switch, a display light and others are provided on the lower part.

In this embodiment, by joining the television camera apparatus 3 and the light source apparatus 4 together, the whole apparatus can be designed to be small and also the operability of the apparatus can be improved.

The other formations, operations and effects are the same as in the first embodiment.

As stated above, according to the present invention, the apparatus has a simple formation and is easily operated for attaching and removing, and the optical axis of the image guide can accurately correspond to the optical axis of the object image observing means. Also, the end surface of the image guide can be accurately placed in the focal position of the forming image lens system of the object image observing means according to the present invention.

What is claimed is:

1. An endoscope connecting system comprising:
   an elongated inserting part for insertion into a tubular cavity, said elongated inserting part having a tip part and a base end part;
   an objective optical system provided at said tip part;
   an image guiding means, extending from a focal position of said objective optical system at an incident end surface to said base end part at an emitting surface, for transmitting an object image;
   a connector connected to said base end part of said elongated inserting part;
   an object image observing means having a connector receiving part detachably connected to said connector, and an image forming lens system for making the object image able to be observed;
   a taper surface formed on at least one of said connector and said connector receiving part where said connector and said connector receiving part abut; and
   a pressing means, located in said connector receiving part, for placing an emitting end surface of said image guiding means in a focal position of said image forming lens system of said object image observing means by pressing said connector toward said connector receiving part when said connector is connected to said connector receiving part and for making an optical axis of said image guiding means correspond with an axis of said object image observing means.

2. The apparatus of claim 1 wherein said image guiding means includes an image guiding cable which is inserted into said connector.

3. The apparatus of claim 1 wherein said object image observing means includes a solid state imaging device for imaging the object image and converting the object into an electric signal.

4. The apparatus of claim 1 wherein said pressing means is provided in the object image observing means, said object image observing means including
   a tubular member having an opening in which said connector can be inserted and a cam groove slit from an end of said opening;
   a ring slidably provided on an outer circumference of said tubular member and having a cam groove notched at a side toward the end of said opening; and
   a pushing means of said ring pushing said ring in an axial direction.

5. The apparatus of claim 4 wherein said cam groove slit of said tubular member has a first groove extending obliquely in the axial direction and a second groove connected to said first groove and extending in the axial direction.

6. The apparatus of claim 4 wherein said cam groove of said ring includes a first groove extending obliquely in the axial direction and has a second groove extending in a circumference direction of said ring.

7. The apparatus of claim 4 wherein said connector has a projection provided in a direction perpendicular to the axial direction, said projection is placed in the cam groove provided in said tubular member and said ring.

8. The apparatus of claim 1 wherein said connector has a light guiding connector in which illuminating light from a light source enters.

9. The apparatus of claim 1 wherein said object image observing means is an eyepiece part having said pressing means.

10. An endoscope connecting system comprising:
    an elongated inserting part for insertion into a tubular cavity, said elongated inserting part having a tip part and a base end part;
    an objective optical system provided at said tip part;
    an image guiding means, extending from a focal position of said objective optical system at an incident end surface to said base end part at an emitting end surface, for transmitting an object image;
    a connector connected to said base end part, said connector having a projection part projecting outward from an outer circumference of said connector;
    an object image observing means having a connector receiving part detachably connected to said connector, and an image forming lens system for making said object image able to be observed; and
    a pressing means, located in said connector receiving part, for placing an emitting end surface of said image guiding means in said focal position of said image forming lens system by pressing said connector toward said connector receiving part when said connector is connected to said connector receiving part and for making an optical axis of said image guiding means correspond with an axis of said object image observing means, said pressing means including
    a tubular part having a cam groove extending obliquely with respect to an axial direction of said connector receiving part and then extending in the axial direction for guiding said projection part of said connector, and a ring-like part, provided on an outer circumference of said tubular part, having a cam groove extending obliquely to said tubular part and said ring-like part being movable in the axial direction of said tubular part, said ring-like part guiding the projection part of said connector, wherein said pressing means pressing said ring-like part toward said tubular part.

* * * * *